(12) United States Patent
Sapienza

(10) Patent No.: US 8,292,158 B2
(45) Date of Patent: Oct. 23, 2012

(54) LOCKING MECHANISM FOR USE WITH LOADING UNITS

(75) Inventor: Jonathan W. Sapienza, West Haven, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 13/465,242

(22) Filed: May 7, 2012

(65) Prior Publication Data

US 2012/0217284 A1 Aug. 30, 2012

Related U.S. Application Data

(62) Division of application No. 12/615,294, filed on Nov. 10, 2009, now Pat. No. 8,186,558.

(51) Int. Cl.
*A61B 17/068* (2006.01)

(52) U.S. Cl. ............... 227/180.1; 227/175.1; 227/176.1; 227/177.1; 227/19; 403/326; 606/219

(58) Field of Classification Search ............... 227/180.1, 227/175.1, 177.1, 19; 403/326; 606/219
See application file for complete search history.

(56) References Cited

U.S. PATENT DOCUMENTS

| | | | |
|---|---|---|---|
| 4,577,367 A | 3/1986 | Durand | |
| 5,588,329 A | 12/1996 | Nedachi | |
| 5,664,792 A | 9/1997 | Tseng | |
| 5,752,644 A | 5/1998 | Bolanos et al. | |
| 5,782,396 A | 7/1998 | Mastri et al. | |
| 6,059,598 A | 5/2000 | Yamashita et al. | |
| 6,109,500 A | 8/2000 | Alli et al. | |
| 6,656,193 B2 | 12/2003 | Grant et al. | |
| D509,589 S | 9/2005 | Wells | |
| 6,953,139 B2 | 10/2005 | Milliman et al. | |
| 6,974,462 B2 | 12/2005 | Sater | |
| 6,988,649 B2 | 1/2006 | Shelton, IV et al. | |
| 7,000,818 B2 | 2/2006 | Shelton, IV et al. | |
| 7,044,352 B2 | 5/2006 | Shelton, IV et al. | |
| 7,055,730 B2 | 6/2006 | Ehrenfels et al. | |
| 7,055,731 B2 | 6/2006 | Shelton, IV et al. | |
| 7,128,253 B2 | 10/2006 | Mastri et al. | |
| 7,131,978 B2 | 11/2006 | Sancoff et al. | |
| 7,140,528 B2 | 11/2006 | Shelton, IV | |
| 7,143,926 B2 | 12/2006 | Shelton, IV et al. | |
| 7,159,750 B2 | 1/2007 | Racenet et al. | |
| 7,328,828 B2 | 2/2008 | Ortiz et al. | |
| 7,380,696 B2 | 6/2008 | Shelton, IV et al. | |
| 7,565,993 B2 | 7/2009 | Milliman et al. | |
| 7,604,150 B2 | 10/2009 | Boudreaux | |
| 7,694,864 B2 | 4/2010 | Okada et al. | |
| 2008/0041916 A1 | 2/2008 | Milliman et al. | |

*Primary Examiner* — Lindsay Low
*Assistant Examiner* — Michelle Lopez

(57) ABSTRACT

A loading unit configured for engagement with a surgical instrument having a firing rod is disclosed. The loading unit comprises a proximal body portion, a tool assembly, and a knife assembly. The tool assembly is disposed in mechanical cooperation with the proximal body portion. The knife assembly is movably disposed at least partially within the proximal body portion and includes a proximal end positioned to engage the firing rod, and includes a first arm and a second arm. The first arm is biased towards the longitudinal axis via a biasing force. The biasing force is selected to allow the first arm to deflect when the firing rod is advanced. The first arm and the second arm of the knife assembly are configured to engage a firing rod of a surgical instrument as the surgical instrument is being actuated.

10 Claims, 10 Drawing Sheets

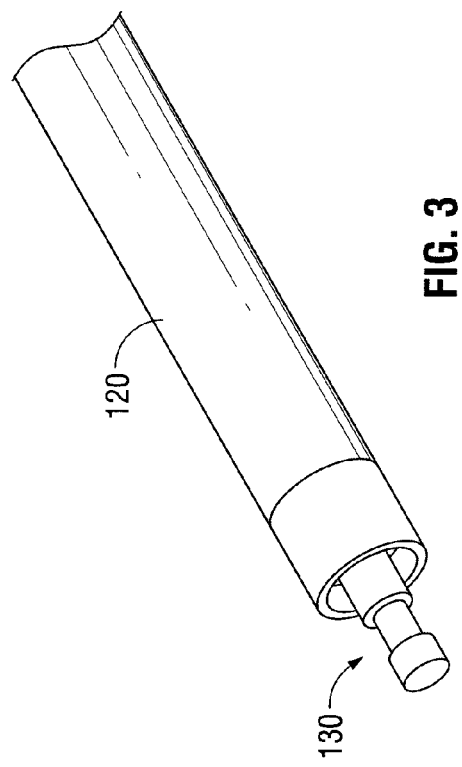
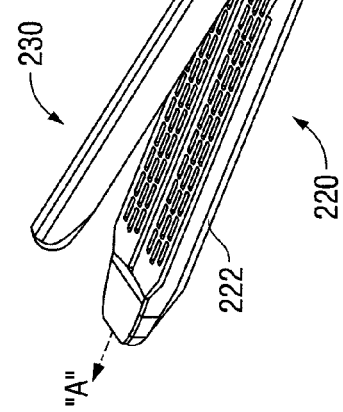
FIG. 3
FIG. 4

500 # LOCKING MECHANISM FOR USE WITH LOADING UNITS

CROSS-REFERENCE TO RELATED APPLICATIONS

This application is a divisional of U.S. application Ser. No. 12/615,294 filed Nov. 10, 2009, now U.S. Pat. No. 8,186,558, and the disclosures of each of the above-identified applications are hereby incorporated by reference in their entirety.

BACKGROUND

1. Technical Field

The present disclosure relates generally to instruments for surgically joining tissue and, more specifically, to a loading unit having a locking mechanism for use with a surgical instrument.

2. Background of Related Art

Various types of surgical instruments used to surgically join tissue are known in the art, and are commonly used, for example, for closure of tissue or organs in transection, resection, anastomoses, for occlusion of organs in thoracic and abdominal procedures, and for electrosurgically fusing or sealing tissue.

One example of such a surgical instrument is a surgical stapling instrument, which may include an anvil assembly, a cartridge assembly for supporting an array of surgical staples, an approximation mechanism for approximating the cartridge and anvil assemblies, and a firing mechanism for ejecting the surgical staples from the cartridge assembly.

Using a surgical stapling instrument, it is common for a surgeon to approximate the anvil and cartridge members. Next, the surgeon can fire the instrument to emplace staples in tissue. Additionally, the surgeon may use the same instrument or a separate instrument to cut the tissue adjacent or between the row(s) of staples.

Additionally, a single use loading ("SULU") or a disposable loading unit ("DLU") may be attached to an elongated or endoscopic portion of a surgical stapling instrument. Such loading units allow surgical stapling instruments to have greater versatility, for example. The loading units may be configured for a single use, and/or may be configured to be used more than once.

SUMMARY

The present disclosure relates to a loading unit configured for engagement with a surgical instrument having a firing rod. The loading unit comprises a proximal body portion, a tool assembly, and a knife assembly. The proximal body portion defines a longitudinal axis. The tool assembly is disposed in mechanical cooperation with the proximal body portion. The knife assembly is movably disposed at least partially within the proximal body portion and includes a proximal end positioned to engage the firing rod, and includes a first arm and a second arm. The first arm is biased towards the longitudinal axis via a biasing force. The biasing force is selected to allow the first arm to deflect when the firing rod is advanced. The first arm and the second arm of the knife assembly are configured to engage a firing rod of a surgical instrument as the surgical instrument is being actuated.

The present disclosure also relates to a surgical stapling instrument comprising a handle assembly, a firing rod, an endoscopic portion, a loading unit, and a knife assembly. The handle assembly includes a movable handle. The firing rod is disposed in mechanical cooperation with the movable handle. The endoscopic portion extends distally from the handle assembly. The loading unit is mechanically engageable with the endoscopic portion and includes a proximal body portion defining a longitudinal axis, and a tool assembly. The knife assembly is movably disposed at least partially within the proximal body portion of the loading unit and includes a proximal end positioned to engage the firing rod, and includes a first arm and a second arm. The first arm is biased towards the longitudinal axis via a biasing force selected to allow the first arm to deflect when the firing rod is advanced. The first arm and the second arm of the knife assembly are configured to engage the firing rod as the surgical instrument is being actuated.

BRIEF DESCRIPTION OF FIGURES

Various embodiments of the presently disclosed surgical instruments and loading units are disclosed herein with reference to the drawings, wherein:

FIG. 3 is a perspective view of a distal portion of the handle portion of FIG. 2;

FIG. 4 is a perspective view of a loading unit of the surgical stapling instrument of FIG. 1;

DETAILED DESCRIPTION

Figure 1A:
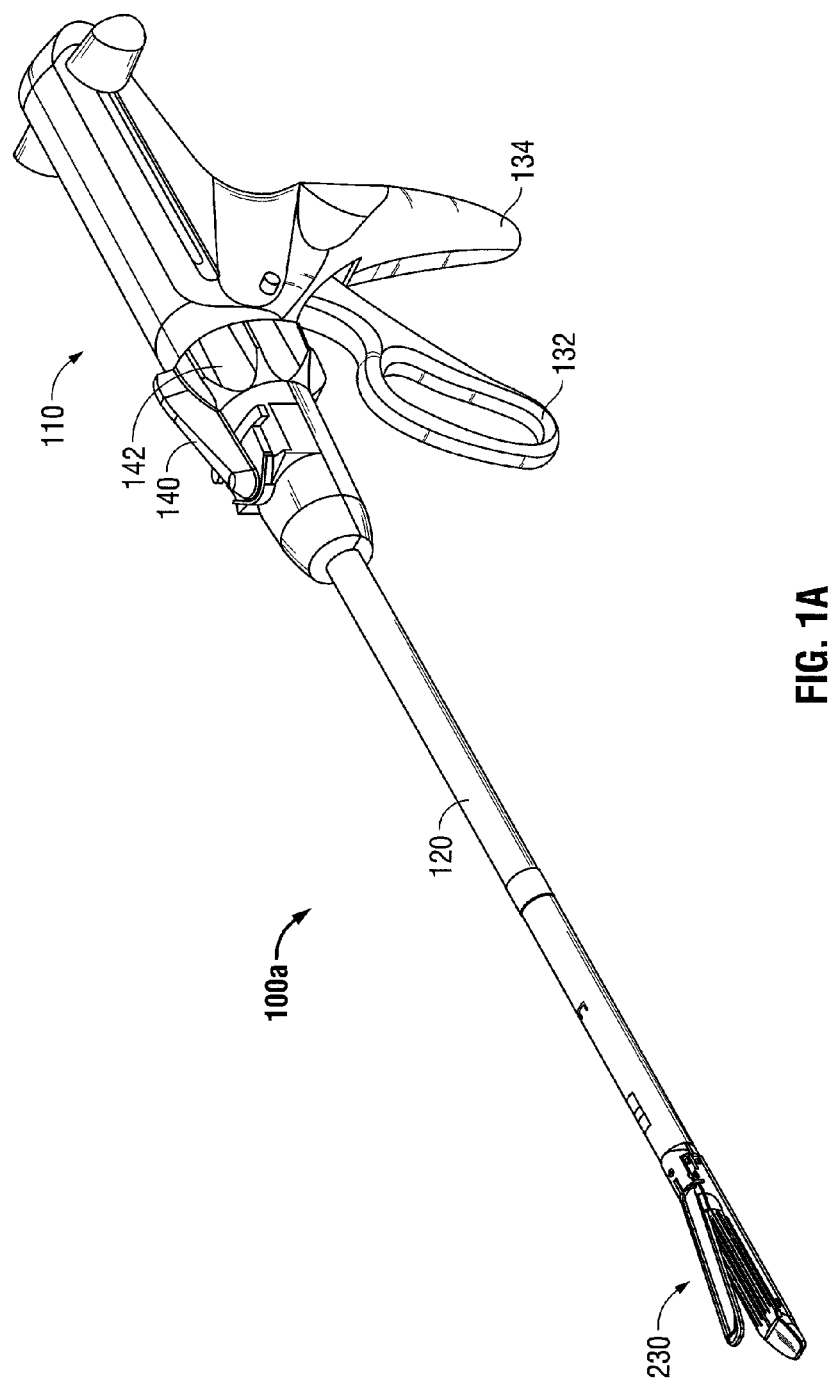
FIG. 1A is a perspective view of a surgical stapling instrument in accordance with the present disclosure.

Embodiments of the presently disclosed surgical instrument, and loading unit for use therewith, are described in detail with reference to the drawings, wherein like reference numerals designate corresponding elements in each of the several views. As is common in the art, the term "proximal" refers to that part or component closer to the user or operator, e.g., surgeon or physician, while the term "distal" refers to that part or component farther away from the user.

Figure 1B:
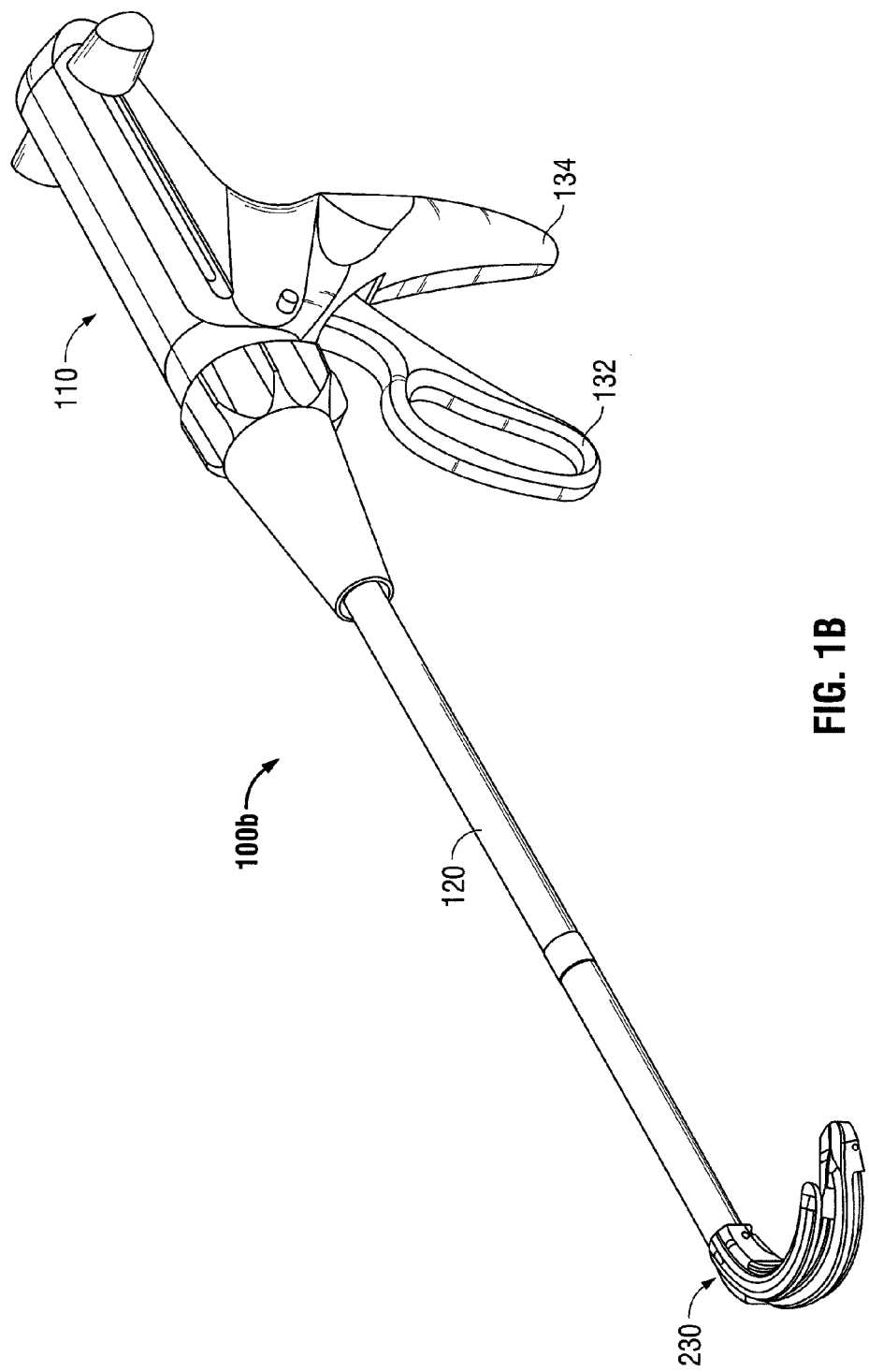
FIG. 1B is a perspective view of another surgical stapling instrument in accordance with the present disclosure.

A surgical stapling instrument having linear jaw members of the present disclosure is indicated as reference numeral 100a in FIG. 1A. A surgical stapling instrument having curved jaw members of the present disclosure is indicated as reference numeral 100b in FIG. 1B. Collectively, surgical stapling instruments 100a and 100b are referred to herein as reference numeral 100. Similarly, several features that are common to both surgical stapling instruments 100a and 100b are collectively referred to as the same reference number (e.g., handle portion 110, endoscopic portion 120, and jaw members 230).

Figure 2:
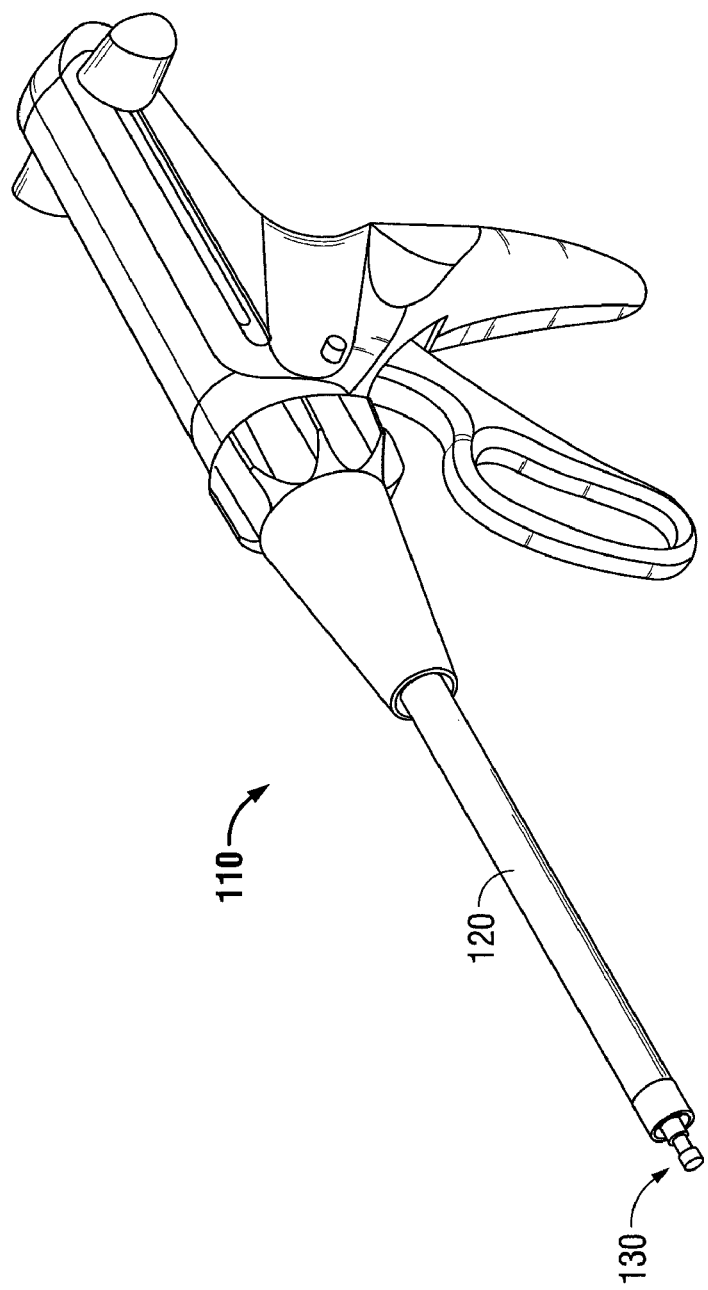
FIG. 2 is a perspective view of a handle portion of the surgical stapling instrument of FIG. 1.

Handle portion 110 of surgical stapling instrument 100 is shown in FIG. 2, and an enlarged view of the distal end of handle portion 110, including a distal end of firing rod 130, is shown in FIG. 3. A single use loading unit ("SULU") or a disposable loading unit ("DLU") (collectively referred to as "loading unit 200"), which is mechanically engageable with handle portion 100 is shown in FIG. 4. Loading unit 200 is attachable to endoscopic portion 120 of surgical stapling instrument 100, e.g., to allow surgical stapling instrument 100 to have greater versatility. Loading unit 200 may be configured for a single use, and/or may be configured to be used more than once.

Examples of loading units for use with a surgical stapling instrument are disclosed in commonly-owned U.S. Pat. No. 5,752,644 to Bolanos et al., the entire contents of which are hereby incorporated by reference herein. Further details of an endoscopic surgical stapling instrument are described in detail in commonly-owned U.S. Pat. No. 6,953,139 to Milliman et al., the entire contents of which are hereby incorporated by reference herein.

Generally, jaw members 230 of loading unit 200 include a cartridge assembly 222 and an anvil assembly 224. Cartridge assembly 222 houses a plurality of staples or fasteners (not explicitly shown in the illustrated embodiments). Cartridge assembly 222 includes a plurality of staple pushers for ejecting the staples therefrom. Anvil assembly 224 includes staple pockets (not explicitly shown in the illustrated embodiments) that are configured to form the staples as they are driven from cartridge assembly 222.

Loading unit 200 may include a plurality of cam bars for interacting with the pushers to deploy the surgical fasteners. For example, the apparatus disclosed in U.S. Pat. No. 5,318,221, the disclosure of which is hereby incorporated by reference herein, in its entirety, has a cam bar adapter that holds a plurality of cam bars and a knife. In this example, a firing rod is advanced through operation of the handle of the apparatus, which drives the cam bars and knife forward. A clamp tube that surrounds the proximal end of the anvil is advanced to clamp the anvil and cartridge together. In another example, the apparatus disclosed in U.S. Pat. No. 5,782,396, the disclosure of which is hereby incorporated by reference herein, in its entirety, has an actuation sled. In this example, an elongated drive beam is advanced distally through operation of the handle of the apparatus, driving the actuation sled forward. The distal end of the drive beam engages the anvil and the channel that supports the cartridge as the drive beam travels distally, to deploy the staples and clamp the anvil and cartridge together.

In a surgical stapling instrument 100 in accordance with the present disclosure, a firing rod 130 is moved distally through actuation of a movable handle 132 to deploy the staples. For example, referring back to FIGS. 1A and 1B, at least a partial actuation of movable handle 132 with respect a stationary handle 134 translates firing rod 130 longitudinally, such that a knife assembly 240 (FIG. 5) translates longitudinally, to approximate at least one jaw member with respect to the other and to eject surgical fasteners (e.g., staples) from cartridge assembly 222 and/or to advance a cutting blade to cut tissue. It is also envisioned that other types of handles can be used such as, for example, motor-driven, hydraulic, ratcheting, etc.

With reference to FIG. 4, loading unit 200 of the present disclosure is shown. Loading unit 200 includes a proximal body portion 210 defining a longitudinal axis "A-A," and a tool assembly 220 including a pair of jaw members 230. Proximal body portion 210 is configured to removably attach to endoscopic portion 120 of surgical instrument 100. More particularly, an insertion tip 202 of loading unit 200 is linearly inserted into the distal end of endoscopic portion 120 (FIGS. 2 and 3) of surgical stapling instrument 100. Nubs 204 of insertion tip 202 (FIG. 4) move linearly through slots (not shown) formed in the distal end of endoscopic portion 120. Subsequently, loading unit 200 is rotated about the longitudinal axis "A-A" such that nubs 204 move transversely through slots (not shown) within endoscopic portion 120. Additionally, during engagement of loading unit 200 and endoscopic portion 120, firing rod 130 of handle portion 110 engages knife assembly 240 of loading unit 200.

Figure 5:
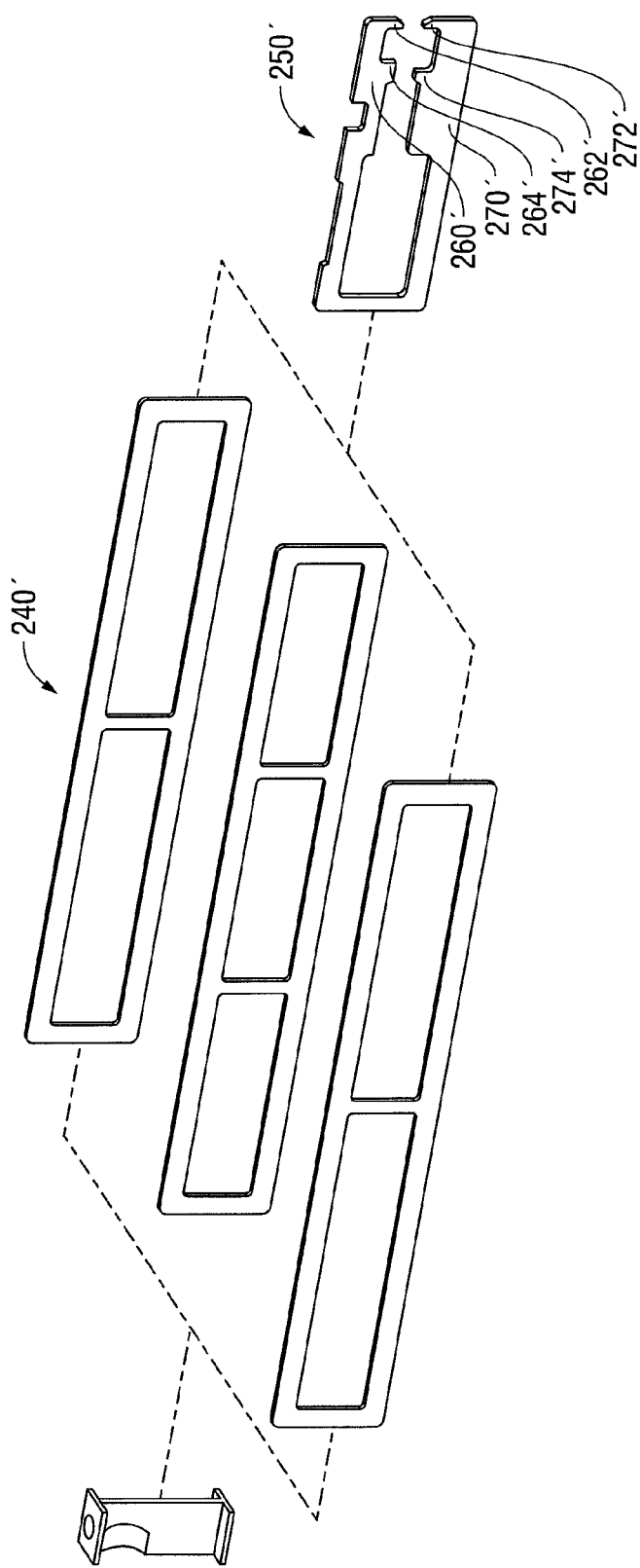
FIG. 5 is a perspective view of a conventional knife assembly of a loading unit.

An example of a proximal portion 250' of a comparative knife assembly 240' is illustrated in FIG. 5. As shown, proximal portion 250' includes a first arm 260' and a second arm 270'. Each of first arm 260' and second arm 270' includes a proximal inwardly extending protrusion 262' and 272', respectively, and a distal inwardly extending protrusion 264' and 274', respectively.

Figure 6:
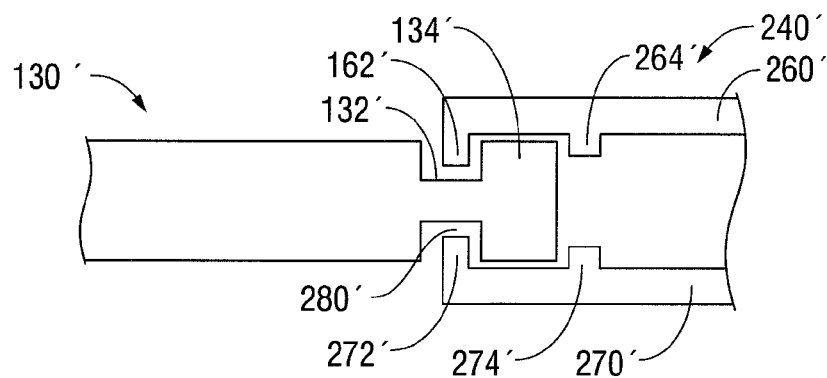
FIG. 6 is a longitudinal cross-sectional view of a portion of a conventional knife assembly of a loading unit engaged with a portion of a conventional firing rod of a surgical stapling instrument.
Figure 7A:
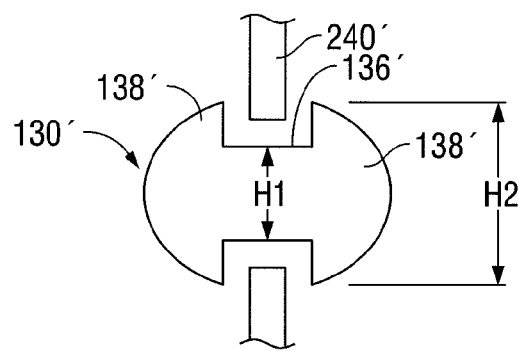
FIGS. 7A and 7B are transverse cross-sectional views of a conventional knife assembly and a conventional firing rod, prior to engagement and while engaged, respectively.
Figure 7B:
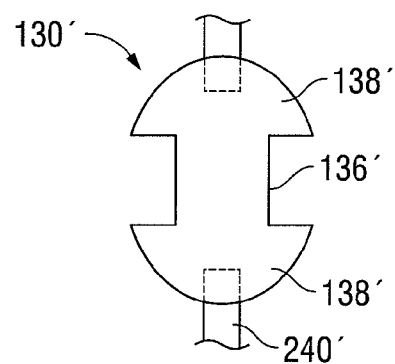
Figure 8:
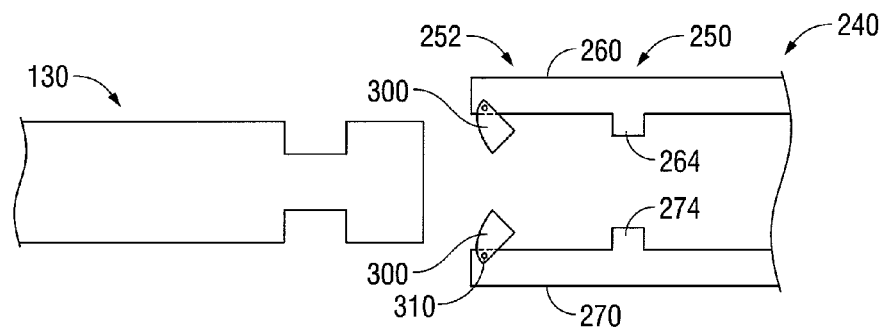
FIG. 8 is a longitudinal cross-sectional view of a knife assembly and a firing rod according to an embodiment of the present disclosure.

FIGS. 6-7B illustrate the engagement between comparative knife assembly 240' and a comparative firing rod 130'. As shown in FIG. 6, comparative firing rod 130' includes a recess 132' therein and a distal lip 134'. Lip 134' of comparative firing rod 130' is configured to fit between proximal inwardly extending protrusions 262', 272' and distal inwardly extending protrusions 264', 274' of comparative knife assembly 240'.

With particular reference to FIGS. 7A and 7B, where transverse cross-sectional views are shown, firing rod 130' includes an inner portion 136' and a pair of outer portions 138'. As shown, the height H1 of inner portion 136' is smaller than the height 112 of outer portions 138'. With continued reference to FIGS. 7A and 7B, the translation of loading unit 200 (including knife assembly 240') with respect to firing rod 130', as discussed above, is configured to allow distal lip 134' of firing rod 130' to pass through an opening 280' disposed between proximal inwardly extending protrusions 262', 272'. Additionally, the rotation of loading unit 200 (including knife assembly 240') with respect to firing rod 130' is configured to position distal lip 134' between proximal inwardly extending protrusions 262', 272' and distal inwardly extending protrusions 264', 274'. Thus, as can be appreciated, firing rod 130' must be rotated to allow distal lip 134' thereof to be able to physically fit through opening 280' disposed between proximal inwardly extending protrusions 262', 272'. As such, when firing rod 130' and knife assembly 240' are properly engaged, proximal and distal translation of firing rod 130' results in corresponding proximal and distal translation of knife assembly 240'.

With reference to FIGS. 8-11B, firing rod 130 and proximal portion 250 of knife assembly 240 of the present disclosure are illustrated. Similarly to comparative knife assembly 240', knife assembly includes a first arm 260 and a second arm 270, with each of first arm 260 and second arm 270 including distal inwardly extending protrusions 264 and 274, respectively. Additionally, knife assembly 240 includes a locking mechanism. In the embodiments illustrated in FIGS. 8-11B, locking mechanism includes a pair of wing elements 300. Wing elements 300 are disposed adjacent a proximal end 252 of proximal portion 250 of knife assembly 240 and are pivotal therewith.

Figure 11A:
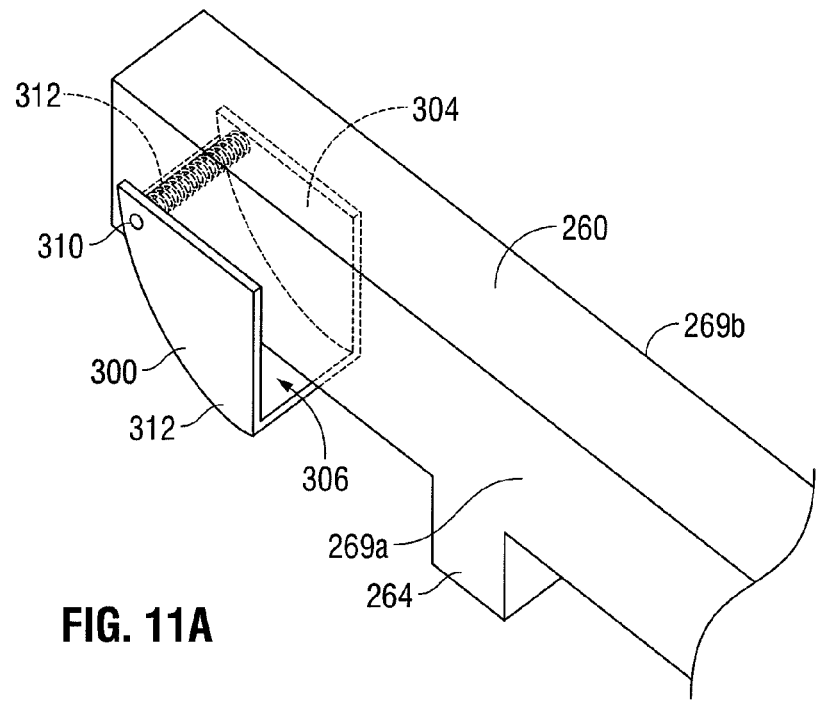
FIGS. 11A and 11B are perspective views of an arm and a wing element in accordance with embodiments of the present disclosure.
Figure 11B:
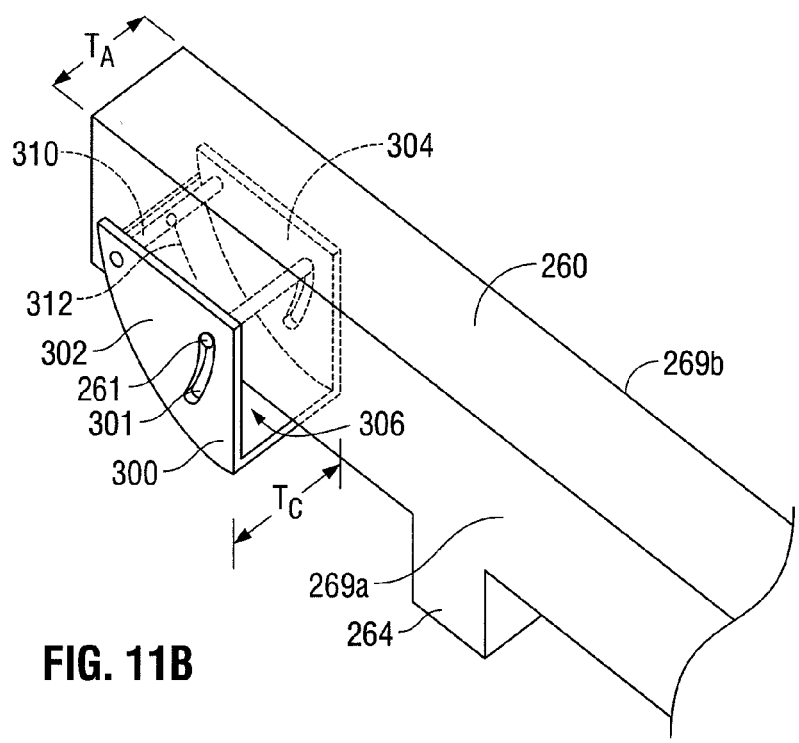

In the illustrated embodiments, wing elements 300 are pivotal about a pivot structure 310 (e.g., a pin or rivet; see FIGS. 11A and 11B). It is envisioned that pivot structure 310 for each wing element 300 extends through its respective first arm 260 or second arm 270. Moreover, with reference to FIGS. 11A and 11B, wing elements 300 are shown having a first side wall 302 and a second side wall 304, which define a channel 306 therebetween. As shown, channel 306 defines a thickness $T_C$, which is wider than a thickness $T_A$ of its associated arm, e.g., first arm 260. Thus, each side wall 302, 304 of wing element 300 can move along sidewalls 269a, 269b of first arm 260. Additionally, in the embodiments illustrated in FIGS. 11A and 11B, wing elements 300 are biased via a biasing element 312 (e.g., a torsion spring (FIG. 11A) or a leaf spring (FIG. 11B)) towards an initial position (FIG. 8), where wing element 300 is spaced from first arm 260, from a second position (FIG. 9), wherein wing element 300 pivoted against first arm 260.

With particular reference to FIG. 11B, first arm 260 includes a pin 261 extending transversely therethrough, and wing element 300 includes an arcuate slot 301 disposed thereon. (It is also envisioned that pin 261 extends from first arm 260.) Pin 261 and slot 301 are configured to mechanically engage one another. It is envisioned that the engagement between pin 261 and slot 301 provides guidance for the travel of wing element 300. Additionally, in the illustrated position, pin 261 acts to limit movement of wing element 300 in the direction provided by biasing element 312.

Figure 9:
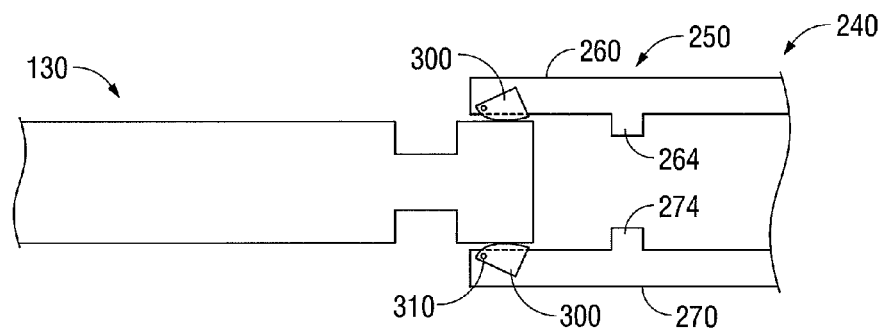
FIG. 9 is a longitudinal cross-sectional view of the knife assembly of FIG. 8 illustrated during engagement with the firing rod of FIG. 8.
Figure 10:
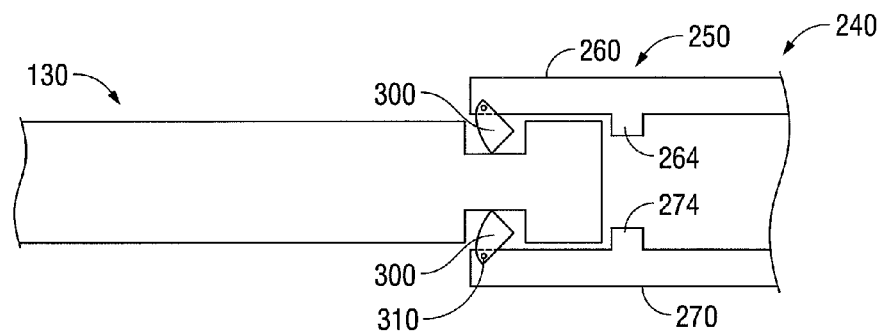
FIG. 10 is a longitudinal cross-sectional view of the knife assembly of FIGS. 8 and 9 engaged with the firing rod of FIGS. 8 and 9.

As can be appreciated with respect to FIGS. 9 and 10, the configuration of knife assembly 240 (including wing elements 300) and firing rod 130 allows distal lip 134 of firing rod 130 to enter the space between wing elements 300 and distal inwardly extending protrusions 264, 274 upon relative longitudinal translation therebetween, and without the need for rotational movement of knife assembly 240 or firing rod 130. More particularly, distal translation of firing rod 130, for example, causes distal lip 134 of firing rod 130 to contact wing elements 300, and to thus cause wing elements 300 to pivot from their initial position (FIG. 8) against the bias of biasing element 312 to their second position (FIG. 9). After distal lip 134 of firing rod 130 translates distally beyond wing elements 300, wing elements 300 are biased back towards their initial position (FIG. 10).

Accordingly, wing elements 300 generally serve the same function as proximal inwardly extending protrusions 262', 272' of comparative knife assembly 240'. However, wing elements 300 are configured to allow knife assembly 240 of loading unit 200 to engage firing rod 130 of endoscopic portion 120 as surgical stapling instrument 100 is being fired. That is, for example, if knife assembly 240 is prematurely advanced and subsequently is not engaged by firing rod 130, distal translation of firing rod 130 would automatically cause firing rod 130 to pivot wing elements 300, and to thus engage with knife assembly 240. As can be appreciated, if a firing rod only pushes a knife assembly without engaging the knife assembly, retraction of the firing rod would not cause retraction of the knife assembly, thus hindering the unlocking or unclamping of the jaw members.

Separation of firing rod 130 from knife assembly 240 (e.g., to remove loading unit 200) is accomplished similarly to comparative firing rod 130' and knife assembly 240', i.e., by rotating loading unit 200 about longitudinal axis "A-A" and longitudinally translating loading unit 200 away from endoscopic portion 120.

Figure 12A:
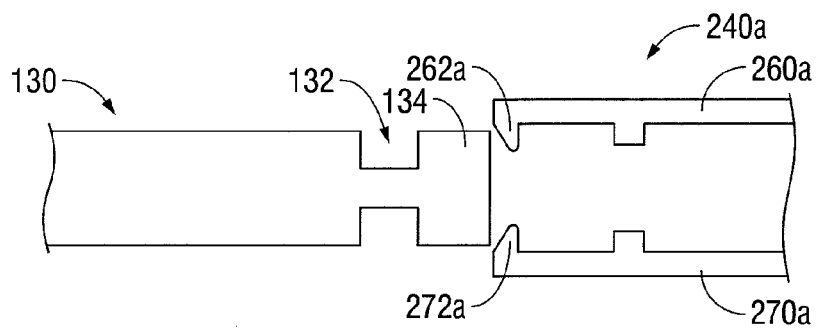
FIG. 12A is a longitudinal cross-sectional view of a firing rod of the present disclosure positioned adjacent a portion of a drive assembly in accordance with an embodiment of the present disclosure.
Figure 12B:
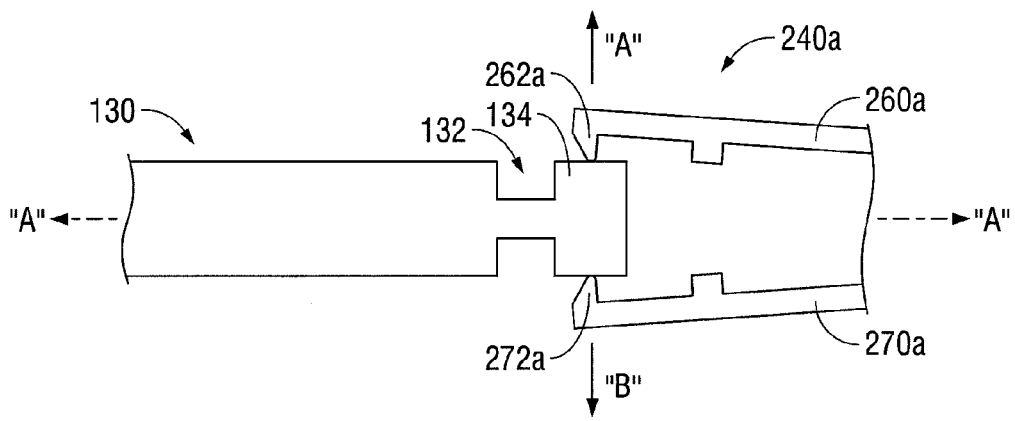
FIG. 12B is a longitudinal cross-sectional view of the firing rod of FIG. 12A engaging the drive assembly of FIG. 12A.
Figure 12C:
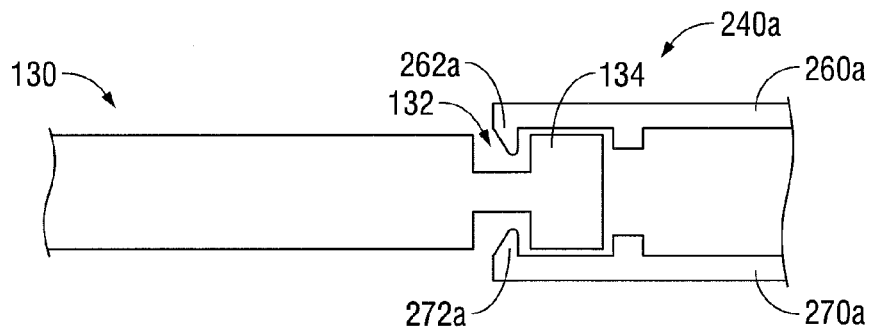
FIG. 12C is a longitudinal cross-sectional view of the firing rod of FIGS. 12A and 12B engaged with the drive assembly of FIGS. 12A and 12B.

With reference to FIGS. 12A-12C, another embodiment of a knife assembly 240a is illustrated. Here, the locking mechanism includes first arm 260a and second arm 270a. Each arm 260a, 270a is configured to flex in the respective directions of arrows "A" and "B" (FIG. 12B). Additionally, each arm 260a, 270a is biased towards the longitudinal axis "A-A." It is envisioned that only a single arm 260a or 270a is biased towards the longitudinal axis "A-A." The flexing and biasing of first arm 260a and/or second arm 270a is accomplished via suitable means. For example, it is envisioned that first arm 260a and/or second arm 270a is made from stainless steel or another suitable biocompatible metal or polymer.

In use, distal translation of firing rod 130 such that distal lip 134 contacts first arm 260a and second arm 270a, causes arms 260a, 270a to flex in the direction of arrows "A" and "B," respectively. After distal lip 134 is translated beyond proximal inwardly extending protrusions 262a, 272a, first and second arms 260a, 270a move in the direction they are biased, i.e., towards the longitudinal axis "A-A," such that proximal inwardly extending protrusions 262a, 272a are within recess 132 of firing rod 130 (FIG. 12C).

Accordingly, the flexible, biased arms 260a and/or 270a of knife assembly 240a function similarly to arms 260, 270 including wing elements 300. That is, arms 260a, 270a are configured to allow knife assembly 240a of loading unit 200 to engage firing rod 130 of endoscopic portion 120 as surgical stapling instrument 100 is being fired.

Accordingly, the flexible, biased arms 260a and/or 270a of knife assembly 240a function similarly to arms 260, 270 including wing elements 300. That is, arms 260a, 270a are configured to allow knife assembly 240a of loading unit 200 to engage firing rod 130 of endoscopic portion 120 as surgical stapling instrument 100 is being fired.

Figure 13A:
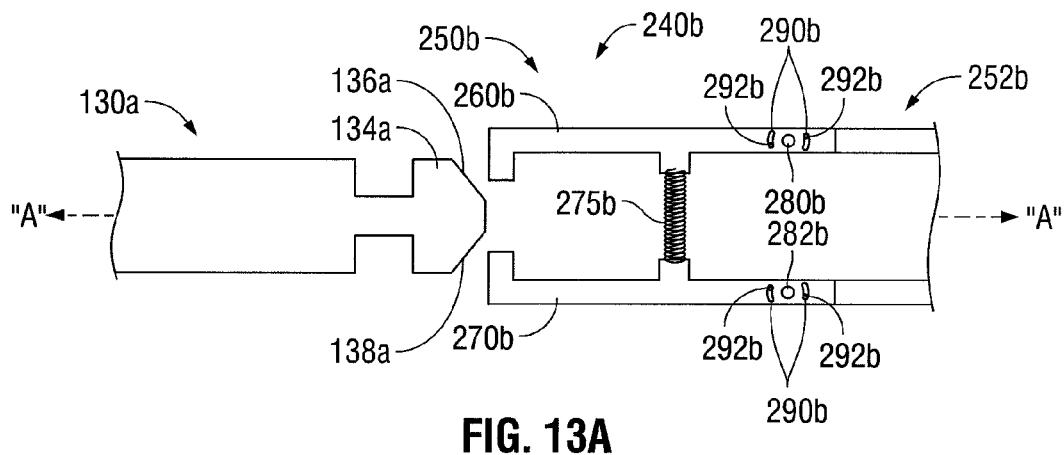
FIG. 13A is a longitudinal cross-sectional view of a firing rod of the present disclosure positioned adjacent a portion of a drive assembly in accordance with an embodiment of the present disclosure.
Figure 13B:
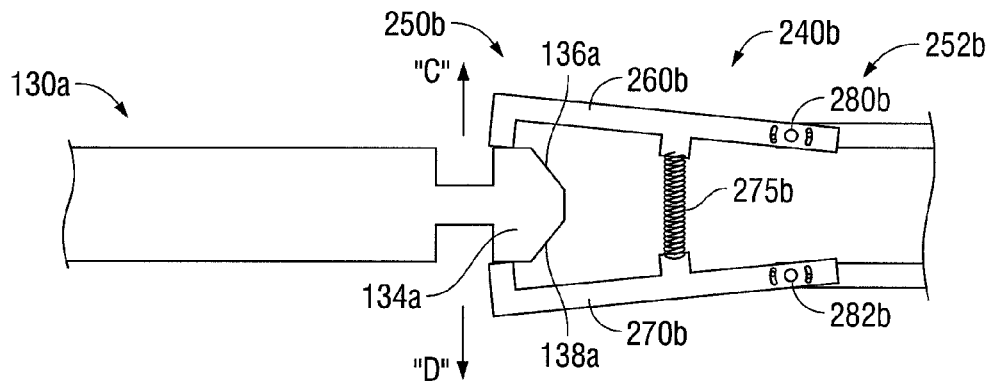
FIG. 13B is a longitudinal cross-sectional view of the firing rod of FIG. 13A engaging the drive assembly of FIG. 13A.
Figure 13C:
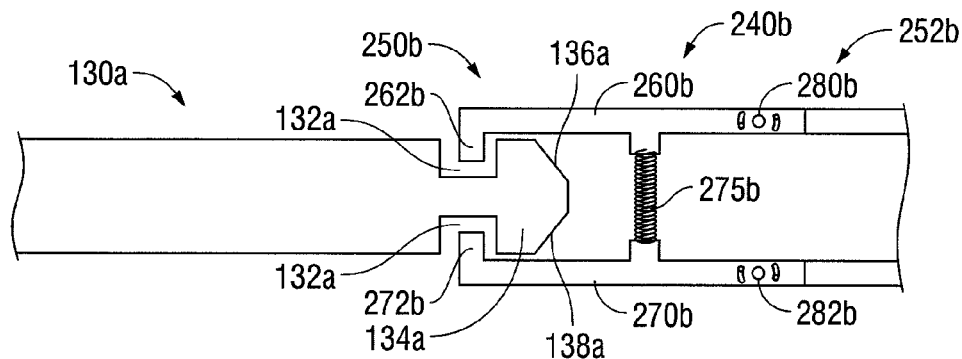
FIG. 13C is a longitudinal cross-sectional view of the firing rod of FIGS. 13A and 13B engaged with the drive assembly of FIGS. 13A and 13B.

With reference to FIGS. 13A-13C, another embodiment of a knife assembly 240b is illustrated. Here, the locking mechanism includes a proximal portion 250b having a first arm 260b, a second arm 270b, and a spring 275b therebetween. Proximal portion 250b is pivotally connected to a distal portion 252b of knife assembly 240b. In particular, at least one of first arm 260b and second arm 270b is pivotally engaged with distal portion 252b. In the illustrated embodiment, first arm 260b is pivotally engaged with distal portion 252b at a first pivot point 280b, and second arm 270b is pivotally engaged with distal portion 252b at a second pivot point 282b. Additionally, proximal portion 250b and distal portion 252b include one of a pair of cam slots 290b and a pair of pins 292b, not necessarily respectively, adjacent each pivot point 280b and/or 282b. As can be appreciated, the inclusion of cam slots 290b and pins 292b help limit the pivotal movement of proximal portion 250b with respect to distal portion 252b.

Each arm 260b, 270b is configured to flex in the respective directions of arrows "C" and "D" (FIG. 13B). Additionally, each arm 260b, 270b is biased towards the longitudinal axis "A-A" via spring 275b. As discussed above, it is also envisioned that only a single arm 260b or 270b is pivotal with respect to distal portion 252b.

In use, distal translation of firing rod 130a such that distal lip 134a thereof contacts first arm 260b and second arm 270b, causes arms 260b and/or 270b to flex in the direction of arrows "C" and "D," respectively. After distal lip 134a is translated beyond proximal inwardly extending protrusions 262b, 272b, first and/or second arms 260b, 270b move in the direction they are biased, i.e., towards the longitudinal axis "A-A," such that proximal inwardly extending protrusions 262b, 272b are within recess 132a of firing rod 130a (FIG. 13C). As shown in FIGS. 13A-13C, distal lip 134a of firing rod 130a includes a pair of angled surfaces 136a, 138a. As can be appreciated, angled surfaces 136a, 138a facilitate the introduction of distal lip 134a distally beyond protrusions 262b, 272b. Additionally or alternatively, a proximal face of proximal inwardly extending protrusions 262b, 272b may include an angled surface, such as protrusions 262a, 272a illustrated in FIGS. 12A-12C.

Accordingly, arms 260b and/or 270b of knife assembly 240b function similarly to arms 260, 270 including wing elements 300 and to arms 260a and 270a. That is, arms 260b, 270b are configured to allow knife assembly 240b of loading unit 200 to engage firing rod 130a of endoscopic portion 120 as surgical stapling instrument 100 is being fired.

It is envisioned that knife assembly 240, 240a, 240b of the present disclosure can be used in combination with an articulatable surgical instrument, e.g., surgical stapling instrument 100a in FIG. 1A. In FIG. 1A, a lever 140 is shown adjacent a rotation dial 142 and may be used to facilitate articulation of jaw members 230. Actuation of lever 140 causes jaw members 230 to move between a first position, where jaw members 230 are substantially aligned with longitudinal axis "A-A," and a second position, where jaw members 230 are disposed at an angle with respect to longitudinal axis "A-A." It is envisioned that moving lever 140 causes an articulation link to move longitudinally, which results in a proximal portion of at least one jaw member moving proximally or distally. That is, moving lever 140 in a first direction causes the articulation link to move proximally (which articulates jaw members 230 in a first direction) and moving lever 140 in a second, opposite direction causes the articulation link to move distally (which articulates jaw members 230 in a second direction). An articulating loading unit for an endoscopic surgical stapler is disclosed in U.S. Pat. No. 6,953,139 to Milliman et al., the entire contents of which have been incorporated by reference herein.

While the above description contains many specifics, these specifics should not be construed as limitations on the scope of the present disclosure, but merely as illustrations of various embodiments thereof. For example, knife assembly 240, 240a, 240b may be configured as a unitary unit, may include multiple layers, and/or may be comprised of several portions (e.g., as shown in FIG. 5). Additionally, it is envisioned that wing elements 300 are disposed on firing rod 130 instead of, or in addition to being disposed on knife assembly 240, 240a, 240b. Further, the present disclosure includes a method of modifying a knife assembly to include pivotable wing elements 300. Therefore, the above description should not be construed as limiting, but merely as exemplifications of various embodiments. Those skilled in the art will envision other modifications within the scope and spirit of the claims appended hereto.

The invention claimed is:

1. A surgical stapling instrument, comprising:
a handle assembly including a movable handle;
a firing rod disposed in mechanical cooperation with the movable handle;
an endoscopic portion extending distally from the handle assembly;
a loading unit being mechanically engageable with the endoscopic portion, the loading unit including a proximal body portion defining a longitudinal axis and a tool assembly; and
a knife assembly movably disposed at least partially within the proximal body portion of the loading unit, the knife assembly including a proximal end positioned to engage the firing rod and having a first arm and a second arm, the first arm being biased towards the longitudinal axis via a biasing force, the biasing force being selected to allow the first arm to deflect when the firing rod is advanced, the first arm and the second arm of the knife assembly being configured to engage the firing rod as the surgical stapling instrument is being actuated.

2. The surgical stapling instrument of claim 1, wherein each of the first and second arms of the knife assembly is biased towards the longitudinal axis.

3. The surgical stapling instrument of claim 1, wherein the first arm of the knife assembly includes a wing element, and wherein the wing element is biased towards the longitudinal axis.

4. The surgical stapling instrument of claim 3, wherein the wing element is biased towards the longitudinal axis via a spring.

5. The surgical stapling instrument of claim 3, wherein the wing element is pivotable with respect to the first arm about a pivot point, wherein the pivot point is disposed on a proximal portion of the wing element, and wherein the pivot point is disposed on a proximal portion of the first arm.

6. The surgical stapling instrument of claim 3, wherein the first arm includes a pin extending transversely therefrom, and wherein the pin is configured to travel within a slot of the wing element.

7. The surgical stapling instrument of claim 1, wherein each of the first and second arms of the knife assembly includes a wing element, and wherein each of the wing elements is biased towards the longitudinal axis.

8. The surgical stapling instrument of claim 7, wherein the firing rod includes at least one recess, and wherein each of the wing elements is configured to engage the at least one recess of the firing rod.

9. The surgical stapling instrument of claim 7, wherein the firing rod includes at least one recess and at least one lip, and wherein each of the wing elements is configured to engage the at least one recess of the firing rod after the wing elements are translated beyond the at least one lip of the firing rod.

10. The surgical stapling instrument of claim 1, wherein engagement between the first arm of the knife assembly and the firing rod of the surgical instrument causes the first arm to deflect away from the longitudinal axis.

* * * * *